US00PP34342P2

(12) United States Plant Patent
Danziger

(10) Patent No.: US PP34,342 P2
(45) Date of Patent: Jun. 14, 2022

(54) ***PETUNIA* PLANT NAMED 'DPETHLOYLW'**

(50) Latin Name: ***Petunia* hybrid**
Varietal Denomination: DPETHLOYLW

(71) Applicant: Danziger 'DAN' Flower Farm, Beit Dagan (IL)

(72) Inventor: Gavriel Danziger, Beit Dagan (IL)

(73) Assignee: Danziger "Dan" Flower Farm

( * ) Notice: Subject to any disclaimer, the term of this patent is extended or adjusted under 35 U.S.C. 154(b) by 0 days.

(21) Appl. No.: 17/550,433

(22) Filed: Dec. 14, 2021

(51) Int. Cl.
*A01H 5/02* (2018.01)
*A01H 6/82* (2018.01)

(52) U.S. Cl.
USPC ..... Plt./356.1

(58) Field of Classification Search
USPC ..... Plt./263.1, 356.1
See application file for complete search history.

*Primary Examiner* — Karen M Redden
(74) *Attorney, Agent, or Firm* — Cassandra Bright

(57) ABSTRACT

A new and distinct *Petunia* plant named 'DPETHLOYLW' is disclosed, characterized by large, abundant, bright golden-yellow flowers. Plants are very branched with a mounded, compact growth habit, and medium vigor. The new variety is a *Petunia*, normally produced as an outdoor garden or container plant.

2 Drawing Sheets

Figure 1:
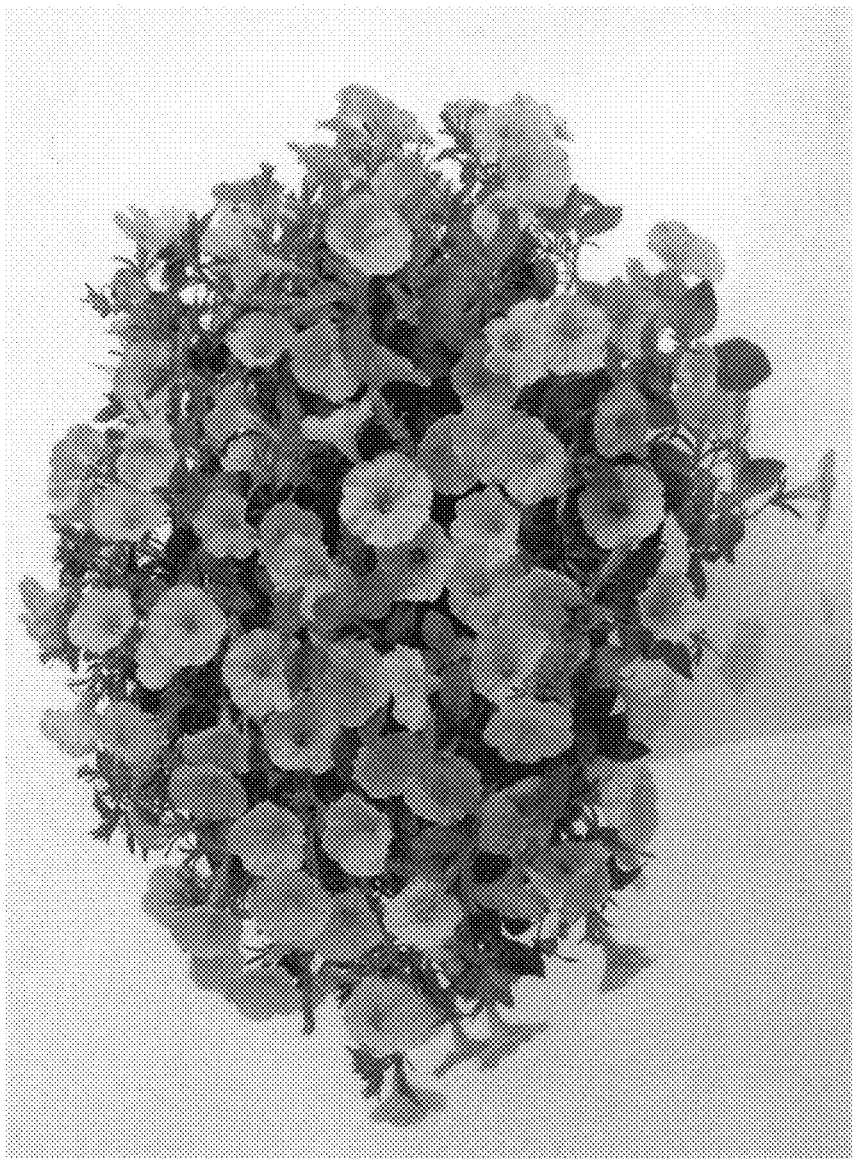

Latin name of the genus and species: *Petunia* hybrid.
Variety denomination: 'DPETHLOYLW'.

BACKGROUND OF THE INVENTION

The new *Petunia* cultivar is a product of a planned breeding program conducted by the inventor, Gavriel Danziger in Moshav Mishmar Hashiva, Israel. The objective of the breeding program was to produce new *Petunia* varieties for ornamental purposes. The crossing resulting in this new variety was made during October of 2018.

The seed parent is the unpatented, propriety variety referred to as *Petunia* 'cv. 17-5610'. The pollen parent is the unpatented, propriety variety referred to as *Petunia* 'cv. 17-6678'. The new variety was discovered in July of 2019 by the inventor in a group of seedlings resulting from the crossing, in a greenhouse in Moshav Mishmar Hashiva, Israel.

Asexual reproduction of the new cultivar 'DPETHLOYLW' was first performed by terminal vegetative cuttings during August of 2019, at a greenhouse in Moshav Mishmar Hashiva, Israel. Subsequent propagation by vegetative cuttings has shown that the unique features of this cultivar are stable and reproduced true to type in more than 6 successive generations.

SUMMARY OF THE INVENTION

The cultivar 'DPETHLOYLW' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPETHLOYLW' These characteristics in combination distinguish 'DPETHLOYLW' as a new and distinct *Petunia* cultivar:

1. Mounded, compact growth habit.
2. Very branched plant with medium vigor.

3. Golden-yellow flower color.
4. Large flowers.
5. Abundant flowering.

PARENT COMPARISON

Plants of the new cultivar 'DPETHLOYLW' are similar to plants of the seed parent in most horticultural characteristics, however, plants of the new cultivar 'DPETHLOYLW' differ in the following:

1. Plant habit of the new variety is mounded and compact; plant habit of the seed parent is a semi-trailing.
2. The new variety is more vigorous than the seed parent.
3. Flower color of the new variety is golden-yellow; flower color of the seed parent is light yellow.
4. The new variety produces larger flowers than the seed parent.
5. The new variety produces more flowers than the seed parent.

Plants of the new cultivar 'DPETHLOYLW' are similar to plants of the pollen parent in most horticultural characteristics, however, plants of the new cultivar 'DPETHLOYLW' differ in the following:

1. Plant habit of the new variety is mounded and compact; plant habit of the pollen parent is a semi-upright.
2. The new variety is more vigorous than the pollen parent.
3. Flower color of the new variety is golden-yellow; flower color of the pollen parent is a lighter golden-yellow.
4. The new variety produces larger flowers than the pollen parent.
5. The new variety produces more flowers than the pollen parent.

COMMERCIAL COMPARISON

Plants of the new cultivar 'DPETHLOYLW' can be compared to the commercial variety *Petunia* 'Capella Soft Yellow', unpatented. These varieties are similar in most horticultural characteristics; however, 'DPETHLOYLW' differs in the following:

1. Flower color of this comparator is light yellow, while flower color of the new variety is golden-yellow.
2. The new variety produces smaller flowers than this comparator.
3. Plants of the new variety are less vigorous than plants of this comparator.

Plants of the new cultivar 'DPETHLOYLW' can also be compared to the patented commercial variety *Petunia* 'Sunshine Ray Imp', unpatented. These varieties are similar in most horticultural characteristics; however, 'DPETHLOYLW' differs in the following:

1. Growth habit of this comparator is upright, while the new variety has a mounded growth habit.
2. Flower color of the comparison variety is yellow, while the new variety has bright golden-yellow flowers.
3. Flowers of the new variety are smaller than flowers of this comparator.

BRIEF DESCRIPTION OF THE PHOTOGRAPHS

The accompanying photograph in FIG. 1 illustrates in full color a typical plant of 'DPETHLOYLW' grown in a 13 cm pot in Moshav Mishmar Hashiva, Israel under moderate Fall conditions.

Figure 2:
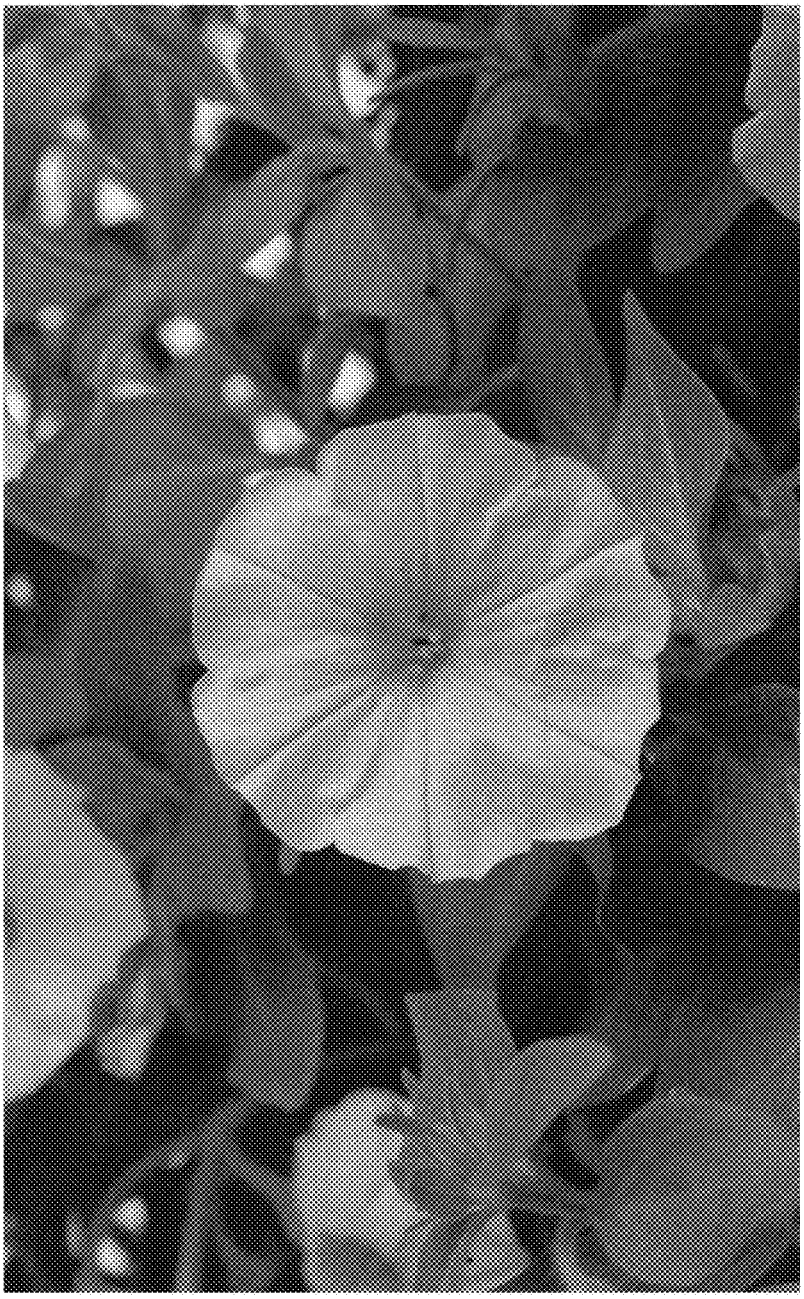

FIG. 2 illustrates in full color a close-up view of a typical flower of 'DPETHLOYLW' grown under the same moderate Fall conditions. Age of the plant photographed is approximately 3 months from a rooted cutting in a 13 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DPETHLOYLW' plants grown in a greenhouse in Moshav Mishmar Hashiva, Israel, under natural lighting. Measurements were taken during spring, summer, and autumn. The plants were approximately 60 days old from a rooted cutting in a 13 cm pot. The growing temperature ranged from approximately 20° C. to 35° C. during the days, 17° C. to 23° C. during the nights. Measurements and numerical values represent averages of typical plant types. Botanical classification: *Petunia* hybrid 'DPETHLOYLW'.

PROPAGATION

Total rooting time: About 10 to 14 days at approximately 20° C.
Root description: Fibrous.

PLANT

Growth habit: Mounded.
Pot size of plant described: 13 cm.
Height: To top of flowers: about 18 cm.
Plant spread: About 40 cm.
Growth rate: Medium.
Branching characteristics:
Length of primary lateral branches: About 20 cm.
Diameter of lateral branches: About 0.3 cm.
Quantity of primary lateral branches: 8.
Characteristics of primary lateral branches:
*Form*.—Cylindrical.
*Diameter*.—About 0.3 cm.
*Color*.—RHS Yellow-Green 144B.
*Texture*.—Pubescent.
*Strength*.—Good.
Internode length: About 1.5 cm.

FOLIAGE

Leaf:
*Arrangement*.—Opposite.
*Quantity*.—Approximately 30 per branch.
*Average length*.—5.5 cm.
*Average width*.—3 cm.
*Shape of blade*.—Elliptic.
*Apex*.—Acute.
*Base*.—Acute.
*Margin*.—Entire.
*Texture of top surface*.—Velvety.
*Texture of bottom surface*.—Pubescent.
*Angle of attachment*.—90°.
*Color*.—Young foliage upper side: RHS Yellow-Green 146A. Young foliage under side: RHS Yellow-Green 146B. Mature foliage upper side: RHS Yellow-Green 146A. Mature foliage under side: RHS Yellow-Green 146B.
*Venation*.—Type: Pinnate. Venation color upper side: RHS Yellow-Green 146C. Venation color under side: RHS Yellow-Green 146D.
*Petiole*.—Length: About 0.8 cm. Diameter: About 0.4 cm. Color: RHS Yellow-Green 146B. Texture: Velvety.

FLOWER

Bloom period: Spring, summer, and autumn.
Days to flowering from rooted cutting: About 30 days.
Inflorescence and flower type and habit: Axillary, single flower, salverform shape, erect habit.
Rate of flower opening: 2 to 3 days from bud to fully opened flower.
Flower longevity on plant: 3-6 days.
Approximate quantity of flowers per plant: About 80.
Persistent or self-cleaning: Self-cleaning.
Bud:
*Shape*.—Tubular.
*Length*.—About 3.8 cm.
*Diameter*.—About 0.7 cm.
*Color*.—RHS Yellow-Green N144A.
Flower size:
*Diameter*.—About 5.5 cm.
*Flower tube length*.—About 2.5 cm.
*Flower tube diameter at distal end*.—About 1.2 cm.
*Flower tube diameter at proximal end*.—About 0.3 cm.
Petals:
*Length from throat*.—About 2 cm.
*Width*.—About 2.5 cm.
*Quantity*.—5.
*Texture*.—Velvety.
*Apex*.—Blunt.
*Margin*.—Entire.

Color:
When opening:
*Upper surface*.—RHS Yellow-Green 151B.
*Lower surface*.—RHS Yellow-Green 151D.
Fully opened:
*Upper surface*.—RHS Yellow-Green 153C.
*Lower surface*.—RHS Yellow-Green 151D.
*Flower throat* (*inside*).—RHS Yellow-Green 153B.
*Flower throat, vein*.—RHS Yellow-Green 144A.
*Flower tube* (*outside*).—RHS Yellow-Green 151D.
*Flower tube, vein*.—RHS Yellow-Green 144A.
Fading:
*Petals fading to*.—RHS Yellow-Green 153B.
Calyx/sepals:
*Quantity per flower*.—5.
*Shape*.—Linear.
*Length*.—About 1.5 cm.
*Width*.—About 0.2 cm.
*Apex*.—Acute.
*Base*.—Cuneate.
*Margin*.—Entire.
*Texture*.—Velvety.
*Color*.—Upper Surface: RHS Yellow-Green 156A.
*Lower surface*.—RHS Yellow-Green 146B.
Pedicel:
*Length*.—About 2.5 cm.
*Diameter*.—About 0.2 cm.
*Color*.—RHS Yellow-Green 146C.
*Orientation*.—45°.
Fragrance: None.

REPRODUCTIVE ORGANS

Stamens:
*Number*.—5.
*Filament length*.—About 2 cm.
Anthers:
*Length*.—About 0.2 cm.
*Shape*.—Rounded.
*Color*.—RHS Green-Yellow 1C.
*Pollen*.—Color: RHS Yellow 4D. Quantity: Plenty.
Pistil:
*Number*.—1.
*Length*.—About 2.2 cm.
*Style*.—Length: About 1.8 cm. Color: RHS Yellow-Green 145B.
*Stigma*.—Shape: Rounded. Color: RHS Yellow-Green 145A. Ovary Color: RHS Green 143C.

OTHER CHARACTERISTICS

Seeds and fruits: About 80 dark brown, rounded seeds of about 0.5 mm diameter, per one, conical capsule.
Disease/pest resistance: Neither resistance nor susceptibility to the normal diseases and pests of *Petunia* have been observed. Pests common to *Petunia* include Aphids and thrips. Typical diseases are *Botrytis* and *Pythium*.
Temperature tolerance: Tolerates a range between 5° C. to 40° C.

What is claimed is:

1. A new and distinct cultivar of *Petunia* plant named 'DPETHLOYLW' as herein illustrated and described.

* * * * *